United States Patent
Sylvia et al.

(10) Patent No.: US 12,042,183 B2
(45) Date of Patent: Jul. 23, 2024

(54) INTEGRAL DOUBLE ROD SPINAL CONSTRUCT

(71) Applicant: NuVasive, Inc., San Diego, CA (US)

(72) Inventors: Ross Sylvia, San Diego, CA (US); Scott Lish, San Diego, CA (US); Robert German, San Diego, CA (US)

(73) Assignee: Nuvasive, Inc., San Diego, CA (US)

( * ) Notice: Subject to any disclaimer, the term of this patent is extended or adjusted under 35 U.S.C. 154(b) by 431 days.

(21) Appl. No.: 17/391,623

(22) Filed: Aug. 2, 2021

(65) Prior Publication Data

US 2021/0353333 A1 Nov. 18, 2021

Related U.S. Application Data

(63) Continuation of application No. 16/268,286, filed on Feb. 5, 2019, now Pat. No. 11,103,283, which is a continuation of application No. 15/440,961, filed on Feb. 23, 2017, now Pat. No. 10,194,949, which is a continuation of application No. PCT/US2017/018898, filed on Feb. 22, 2017.

(60) Provisional application No. 62/298,279, filed on Feb. 22, 2016.

(51) Int. Cl.
*A61B 17/88* (2006.01)
*A61B 17/70* (2006.01)

(52) U.S. Cl.
CPC ...... *A61B 17/7011* (2013.01); *A61B 17/7032* (2013.01); *A61B 17/705* (2013.01)

(58) Field of Classification Search
CPC ............ A61B 17/7055; A61B 17/7044; A61B 17/7011; A61B 17/7032; A61B 17/7059; A61B 17/7022; A61B 17/7037; A61B 17/7007; A61B 17/701; A61B 17/7023; A61B 17/7025; A61B 17/7034; A61B 17/7038; A61B 17/7043; A61B 17/7013; A61B 17/7014; A61B 17/7041; A61B 17/7071; A61B 17/705
USPC ....... 606/246, 250, 261, 262, 264, 265, 266, 606/267, 270, 278, 279, 305, 308, 328
See application file for complete search history.

(56) References Cited

U.S. PATENT DOCUMENTS

| | | | |
|---|---|---|---|
| 4,604,995 A * | 8/1986 | Stephens | A61B 17/7053 606/261 |
| 4,686,970 A * | 8/1987 | Dove | A61B 17/68 606/261 |
| 4,738,251 A * | 4/1988 | Plaza | A61B 17/7053 606/261 |
| 5,129,899 A | 7/1992 | Small et al. | |
| 5,234,431 A | 8/1993 | Keller | |
| 5,330,473 A | 7/1994 | Howland | |
| 5,527,315 A | 6/1996 | Jeanson et al. | |
| 5,702,395 A | 12/1997 | Hopf | |
| 6,136,002 A | 10/2000 | Shih et al. | |
| 6,471,704 B2 | 10/2002 | Gertzbein et al. | |
| 6,524,311 B2 | 2/2003 | Gaines, Jr. | |
| 6,648,885 B1 | 11/2003 | Friesem | |
| 6,689,133 B2 | 2/2004 | Morrison et al. | |
| 7,220,262 B1 | 5/2007 | Hynes | |

(Continued)

FOREIGN PATENT DOCUMENTS

WO  95/08298 A1  3/1995

*Primary Examiner* — Eduardo C Robert
*Assistant Examiner* — David C Comstock

(57) ABSTRACT

An integral dual rod spinal construct for immobilizing and stabilizing vertebral bodies of the spine is described.

18 Claims, 3 Drawing Sheets

(56) References Cited

U.S. PATENT DOCUMENTS

| | | | |
|---|---|---|---|
| 8,062,341 B2 | 11/2011 | Binder et al. | |
| 8,192,468 B2 | 6/2012 | Biedermann et al. | |
| 8,226,695 B2 | 7/2012 | Moore et al. | |
| 8,361,117 B2 | 1/2013 | Michielli et al. | |
| 8,951,258 B2 | 2/2015 | Peultier et al. | |
| 9,168,068 B2 | 10/2015 | McClintock et al. | |
| 10,194,949 B2 | 2/2019 | Sylvia et al. | |
| 11,103,283 B2 | 8/2021 | Sylvia et al. | |
| 2001/0037111 A1* | 11/2001 | Dixon | A61B 17/701 606/264 |
| 2004/0116931 A1* | 6/2004 | Carlson | A61B 17/7044 606/70 |
| 2005/0010215 A1* | 1/2005 | Delecrin | A61B 17/7011 606/264 |
| 2006/0200136 A1* | 9/2006 | Jackson | A61B 17/7032 606/301 |
| 2007/0225708 A1 | 9/2007 | Biedermann et al. | |
| 2008/0097448 A1 | 4/2008 | Binder et al. | |
| 2009/0076549 A1* | 3/2009 | Lim | A61B 17/7038 606/301 |
| 2010/0036425 A1* | 2/2010 | Barrus | A61B 17/7032 606/301 |
| 2011/0144693 A1 | 6/2011 | Black | |
| 2014/0135840 A1 | 5/2014 | McClintock et al. | |
| 2014/0277163 A1* | 9/2014 | Kretzer | A61B 17/7049 606/278 |
| 2015/0342646 A1* | 12/2015 | Wessels | A61B 17/7041 606/255 |
| 2015/0351804 A1* | 12/2015 | Kishan | A61B 17/7011 606/279 |
| 2016/0270824 A1* | 9/2016 | Binder | A61B 17/7059 |

\* cited by examiner

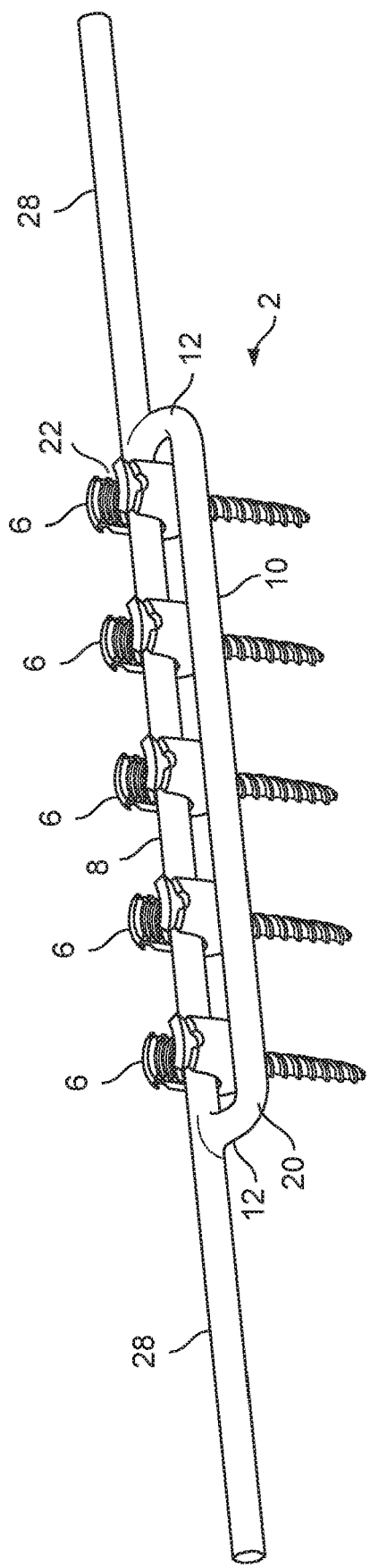
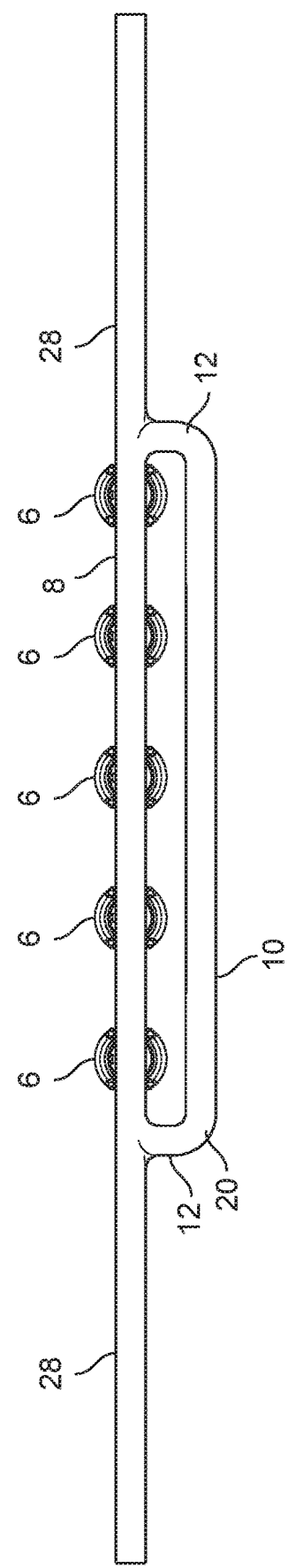
FIG. 3
FIG. 4

INTEGRAL DOUBLE ROD SPINAL CONSTRUCT

CROSS-REFERENCE TO RELATED APPLICATIONS

This patent application is a continuation of U.S. patent application Ser. No. 16/268,286, filed on Feb. 5, 2019, which was a continuation of U.S. patent application Ser. No. 15/440,961, filed on Feb. 23, 2017, now U.S. Pat. No. 10,194,949, which was a continuation of International Pat. App. No. PCT/US17/18898, filed on Feb. 22, 2017, which claims the benefit of U.S. Provisional Application No. 62/298,279, filed on Feb. 22, 2016, the entire disclosure of which is incorporated herein by reference.

BACKGROUND

Field of the Disclosure

The present disclosure relates generally to medical devices, more specifically spinal rods for immobilizing and stabilizing vertebral bodies of the spine.

Background

The spine is formed of a column of vertebrae that extends between the cranium and pelvis. The three major sections of the spine are known as the cervical, thoracic and lumbar regions. There are 7 cervical vertebrae, 12 thoracic vertebrae, and 5 lumbar vertebrae, with each of the 24 vertebrae being separated from each other by an intervertebral disc. A series of about 9 fused vertebrae extend from the lumbar region of the spine and make up the pelvic region of the vertebral column. These fused vertebrae consist of the sacral and coccygeal region of the vertebral column.

The main functions of the spine are to provide support and protect the spinal cord. Even slight disruptions to either the intervertebral discs or vertebrae can result in serious discomfort due to decompression of nerve fibers either within the spinal cord or extending from the spinal cord. If a disruption to the spine becomes severe enough, damage to a nerve or part of the spinal cord may occur and can result in partial to total loss of bodily functions (e.g., walking, talking, and breathing).

Each year millions of people suffer from back pain arising from defects in the intervertebral disc space. Commonly, surgical interventions directed at promoting fusion across the affected joint are employed to permanently provide long term pain relief to the patient. Typically, such fusion surgeries involve performing a partial or complete discectomy to prepare the disc space, and then implanting a natural or synthetic intervertebral fusion implant within the prepared disc space.

Surgical procedures on the spine (for example, procedures meant to fuse two or more vertebra together) often include the immobilization of two or more vertebra. Immobilizing the vertebrae may be accomplished in many ways (e.g., fixation plates and pedicle screw systems). One of the most common methods for achieving the desired immobilization is through the application of bone anchors (most often introduced into the pedicles associated with the respective vertebra to be fixed) that are then connected by rigid rods locked to each pedicle screw. Pedicle screws generally include an anchor component and a rod-housing component (or "tulip") that is often coupled to the anchor component in a manner that permits angular adjustability of the tulip relative to the anchor component in one or more planes. Once the pedicle screws are implanted in the desired positions, a spinal rod is seated in each tulip and locked in position.

One complication of spinal surgery is failure of the implanted components. Rod failure can occur where rod strength is compromised during bending of the rods to fit patient anatomy, or where the stress loads placed on the rod are too great. Therefore, in some procedures that are known to introduce higher stress to the implanted rod, such as pedicle subtraction osteotomy (PSO), it may be desirable to provide increased strength to the rod to increase stability and support to prevent negative outcomes that can result from rod failure.

It is desirable that an improved rod increase the stiffness and fatigue strength of the construct while having a minimal effect on the ease with which the construct is implanted and/or the amount of hardware needed to enhance the strength of the construct (e.g., in comparison to current techniques employing multiple side-by-side rods connected by a series of connectors). An improved rod as disclosed herein could be used for increased stability of short or long constructs, trauma, or posterior reconstruction, in support of spinal fusion. For example, the improved rod disclosed herein may help reduce the incidence of rod fracture across a PSO or unstable construct.

SUMMARY

The needs above, as well as others, are addressed by embodiments of a dual rod spinal fixation constructs described in this disclosure.

In a first aspect, a spinal fixation construct is disclosed comprising: a first spinal rod; a second spinal rod generally parallel to the first rod; a cephalad arm connecting the first and second rods and integrally formed with the first and second rods; and a caudal arm connecting the first and second rods and integrally formed with the first and second rods.

In a second aspect, a spinal rod fixation construct is disclosed comprising: a dual rod formed as a single unit, a plurality of bone anchors with upstanding arms defining a rod channel, and a plurality of lock screws.

In a third aspect, a dual spinal rod for fixing the relative position of a first vertebra and a second vertebra is disclosed, the dual spinal rod comprising: a first elongate member of generally cylindrical shape having a first cephalad end and a first caudal end, the first elongate member being of a diameter suitable to be seated within a rod channel of a pedicle screw, and being of a length sufficient to connect two adjacent vertebrae; a second elongate member roughly parallel to the first elongate member having a second cephalad end and a second caudal end; a cephalad lateral portion connecting the first cephalad end to the second cephalad end; and a caudal lateral portion connecting the first caudal end to the second caudal end and roughly parallel to the cephalad lateral portion; wherein the dual spinal rod is constructed entirely from a rigid, non-absorbable biocompatible material.

In a fourth aspect, a dual spinal rod for fixing the relative position of a first vertebra and a second vertebra is disclosed, the dual spinal rod comprising: a first elongate member of generally cylindrical shape being of a diameter suitable to be seated within a rod channel of a pedicle screw, and being of a length sufficient to connect two adjacent vertebrae; a second elongate member roughly parallel to the first elongate member having a cephalad end and a caudal end; a cephalad lateral portion connecting the cephalad end of the second elongate member to the first elongate member; and a caudal lateral portion connecting the caudal end of the second elongate member to the first elongate member, and roughly parallel to the cephalad lateral portion; wherein the dual spinal rod is constructed entirely from a rigid, non-absorbable biocompatible material; wherein the first elongate portion extends beyond a point at which it connects to the cephalad lateral portion in a longitudinal direction; and wherein the first elongate portion extends beyond a point at which it connects to the caudal lateral portion in the longitudinal direction.

In a fifth aspect, a method of stabilizing vertebra in a spinal procedure is disclosed, the method comprising: implanting a plurality of bone anchors; seating the first rod of the spinal rod fixation construct in the rod housing of the plurality of bone anchors; and engaging a plurality of lock screws complementary to the bone anchors such that the lock screws secure the spinal rod fixation construct in the rod housing of the plurality of bone anchors.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF DRAWINGS

FIG. 3 is a perspective view of a second embodiment of an integral double rod spinal construct.

FIG. 4 is a top plan view of the integral double rod spinal construct of FIG. 3.

DETAILED DESCRIPTION

Figure 1:
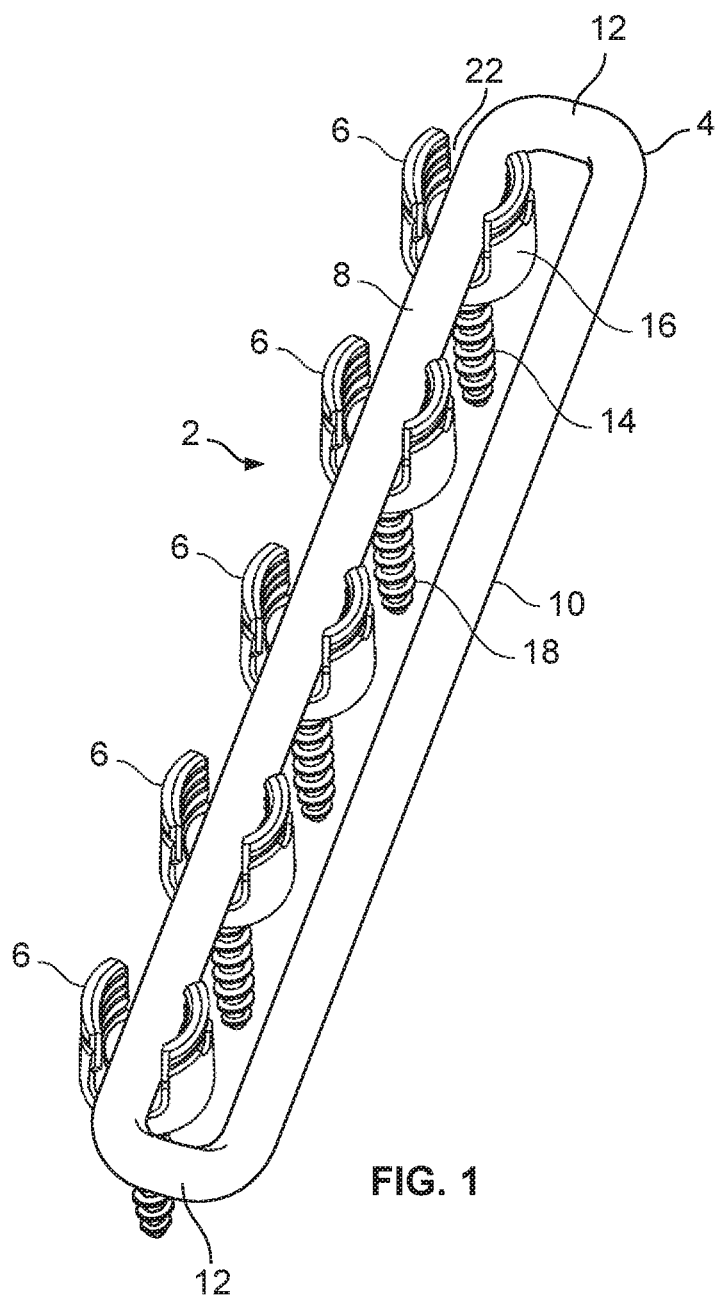
FIG. 1 is a perspective view of one example of an integral double rod spinal construct.

Illustrative embodiments of a system for spinal fixation, parts, and methods for use thereof, are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system for spinal fixation, parts, and methods for use thereof disclosed herein boasts a variety of inventive features and components that warrant patent protection, both individually and in combination.

This disclosure describes several examples of an integral double rod spinal fixation construct suitable for use in spinal fixation procedures. It will be appreciated that the spinal rod fixation construct disclosed may extend any number of levels from a single level construct to a long construct spanning multiple spinal levels and multiple spinal regions from the lumbosacral to cervical regions, and may include any variety of combinations of known anchors, rods and connectors.

By way of example, an integral double rod construct may be particularly beneficial in procedures that introduce higher stress to the implanted rod, such as pedicle subtraction osteotomy (PSO). The integral double rod spinal fixation construct of the present disclosure has several advantages over the prior art osteotomy systems. For example, integrated arms joining the rods may provide for a stiffer construct than a collection of single rods with added connectors, which may lead to less rod failure in PSO. Placement of a single integral double rod is easier, faster, and cheaper than placing four single rods in parallel. Additionally, a construct comprising two rods instead of four rods decreases the metal and material through the fusion bed due to the elimination of two rods and multiple connectors.

A general embodiment of the construct comprises a first spinal rod, a second spinal rod generally parallel to the first rod, and arms at each end formed integrally with, and connecting the first and second rods. The components in the system are constructed from one or more non-absorbable biocompatible materials. Specific examples of such suitable materials include titanium, alloys of titanium, steel, and stainless steel.

While this description refers to "first" and "second," it will be appreciated that such terminology is provided to aid in distinguishing the elements of the rods from one another and should not be read to limit the claims to a particular order or orientation of the dual rod.

In a first general embodiment, a dual spinal rod 2 for fixing the relative position of a first vertebra and a second vertebra comprises a first elongate member of generally cylindrical shape having a cephalad end and a caudal end. In some embodiments, the elongate member may be a first rod 8. The first elongate member may have a diameter suitable to be seated within a rod channel 22 of a pedicle screw. Further, the elongate member may be of a length sufficient to connect two adjacent vertebrae. The dual spinal rod further comprises a second elongate member roughly parallel to the first elongate member. The second elongate member may be a second rod 10. A cephalad lateral portion connects the first and second elongate members at the cephalad end and a caudal lateral portion connects the first and second elongate members at the caudal end. The lateral portion may be an arm 12. The caudal lateral portion is roughly parallel to the cephalad lateral portion. The dual spinal rod is constructed entirely from a rigid, non-absorbable biocompatible material.

In a second general embodiment, a dual spinal rod 2 for fixing the relative position of a first vertebra and a second vertebra comprises a first elongate member of generally cylindrical shape and having a diameter suitable to be seated within a rod channel 22 of a pedicle screw. The first elongate member may be a first rod 8. The first elongate member is of a length sufficient to connect two adjacent vertebrae. The dual rod further comprises a second elongate member roughly parallel to the first elongate member. The second elongate member may be a rod 10. The elongate members are connected at their cephalad end and caudal ends by lateral portions which are roughly parallel to one another. The lateral portions may be arms 12. In some embodiments, the first elongate portion extends beyond a point at which it connects to the cephalad lateral portion in a longitudinal direction. In other embodiments, the first elongate portion extends beyond a point at which it connects to the caudal lateral portion in the longitudinal direction. In yet further embodiments, elongate portions extend longitudinally beyond both the cephalad and caudal lateral portions. In each embodiment, the dual spinal rod is constructed entirely from a rigid, non-absorbable biocompatible material.

Figure 2:
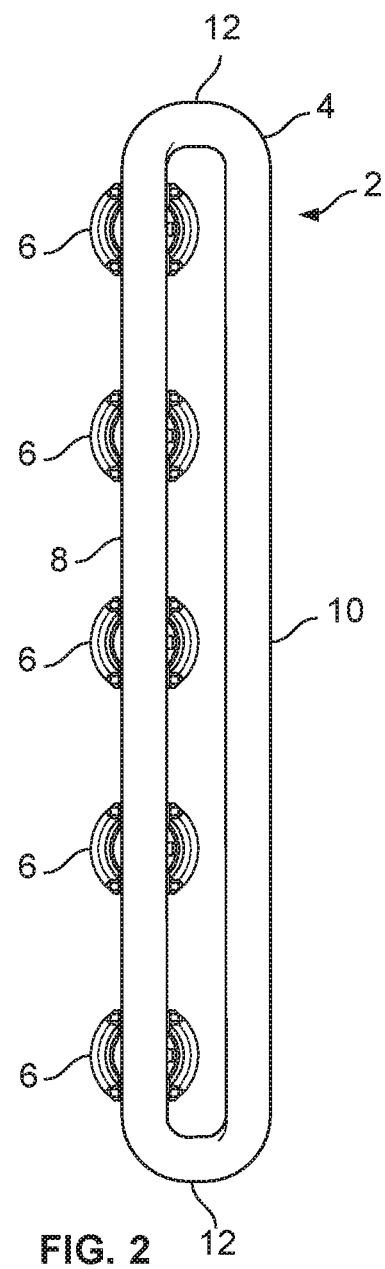
FIG. 2 is a top plan view of the integral double rod spinal construct of FIG. 1.

More specifically, FIGS. 1-2 illustrate one example of an integral double rod spinal fixation construct 2 according to a first embodiment. When implanted in a patient, the rod spinal fixation construct 2 will be oriented in a generally cephalad-caudal orientation. The integral double rod spinal fixation system includes an integral double spinal rod 4 and a plurality of bone anchors 6. The integral double spinal rod 4 includes a first rod 8 and a second rod 10 that is parallel to the first rod 8. The first and second rods 8, 10 are connected to each other at the cephalad and caudal ends by an arm 12 that is integrally formed with the first and second rods 8, 10 such that the first and second rods 8, 10 and arms 12 comprise one single piece of metal. By way of example, the first and second rods 8, 10 and arms 12 may be of uniform thickness. The first rod 8 is configured to engage the bone anchors 6 and is therefore generally cylindrical in shape. The second rod 10 may have any cross-sectional shape, and primarily functions to provide stability and rigidity to the construct, however the second rod portion 10 may also be used as an attachment point for additional hardware or for bending.

The bone anchor 6 may be any bone anchor suitable for use in a fixation procedure, including, without limitation, bone screws or hooks. By way of example, the bone anchor 6 may be a polyaxial pedicle screw as shown in the embodiment of FIG. 1. The bone anchor 6 of the current example includes a shank 14 and a rod-housing 16 coupled to the shank. The shank 14 has a threaded region 18 for purchase into the bone (e.g., a pedicle), a neck, and a head having a spherical undersurface and a drive tool engaging feature. The housing 16 includes a base and a pair of upstanding arms extending from the base parallel to a longitudinal axis of the base. Slots separating the upstanding arms define a rod channel 22 passing through the housing. The arms include tooling attachment features for coupling the housing to various tools useful during implantation of the bone anchor and associated fixation construct (e.g., inserters, reducers, etc.) and locking cap engagement features that cooperate with a locking cap to capture and lock the first rod 8 in the rod channel 22. The base includes a perimeter wall that defines an inner cavity configured to receive the shank head therein and a lower surface with an opening into the inner cavity.

In use, after the osteotomy procedure has progressed to the point where bone has been removed and the surgeon needs to stabilize the spine, the first step is to implant the bone anchors 6 into the desired places on the remaining bony structure. The integral double rod 4 is then placed in position by seating the first rod 8 in the rod housing 16 of the bone anchor 6. The integral double rod 4 may be placed such that the second rod 10 is oriented either medially or laterally of the first rod 8. Any bending of the rod construct 2 that is necessary to have the first rod 8 seat properly would occur at this time. A unique rod bender (not shown) may be provided that is capable of bending both rods 8, 10 at the same time and to the same degree. After the integral double rod 4 has been properly placed, it is locked into position by engaging a plurality of lock screws with the housings 16 of the bone anchors 6.

FIGS. 3-4 illustrate an example of an integral double rod spinal fixation system 2 according to a second embodiment. The integral double rod spinal fixation system includes an integral double spinal rod 20 and a plurality of bone anchors 6. The integral double spinal rod 20 of the second example includes a first rod 8 and a second rod 10 that is parallel to the first rod 8. The first and second rods 8, 10 are connected to each other by an arm 12 that is integrally formed with the first and second rods 8, 10 such that the first and second rods 8, 10 and arms 12 comprise one single piece of metal. By way of example, the arms 12 are located at each end of the second rod 10 and extend laterally to connect with the first rod 8. By way of example, the first and second rods 8, 10 and arms 12 may be of uniform thickness. The first rod 8 is configured to engage the bone anchors 6 and is therefore generally cylindrical in shape. The first rod 8 further includes rod extensions 28 extending longitudinally from either end of the first rod 8. The rod extensions 28 enable connection to additional hardware in longer spine stabilization constructs, for example, larger deformity or trauma cases. The second rod 10 may have any cross-sectional shape, and primarily functions to provide stability and rigidity to the construct, however, the second rod 10 may also be used as an attachment point for additional hardware or for bending, etc.

Figure 5:
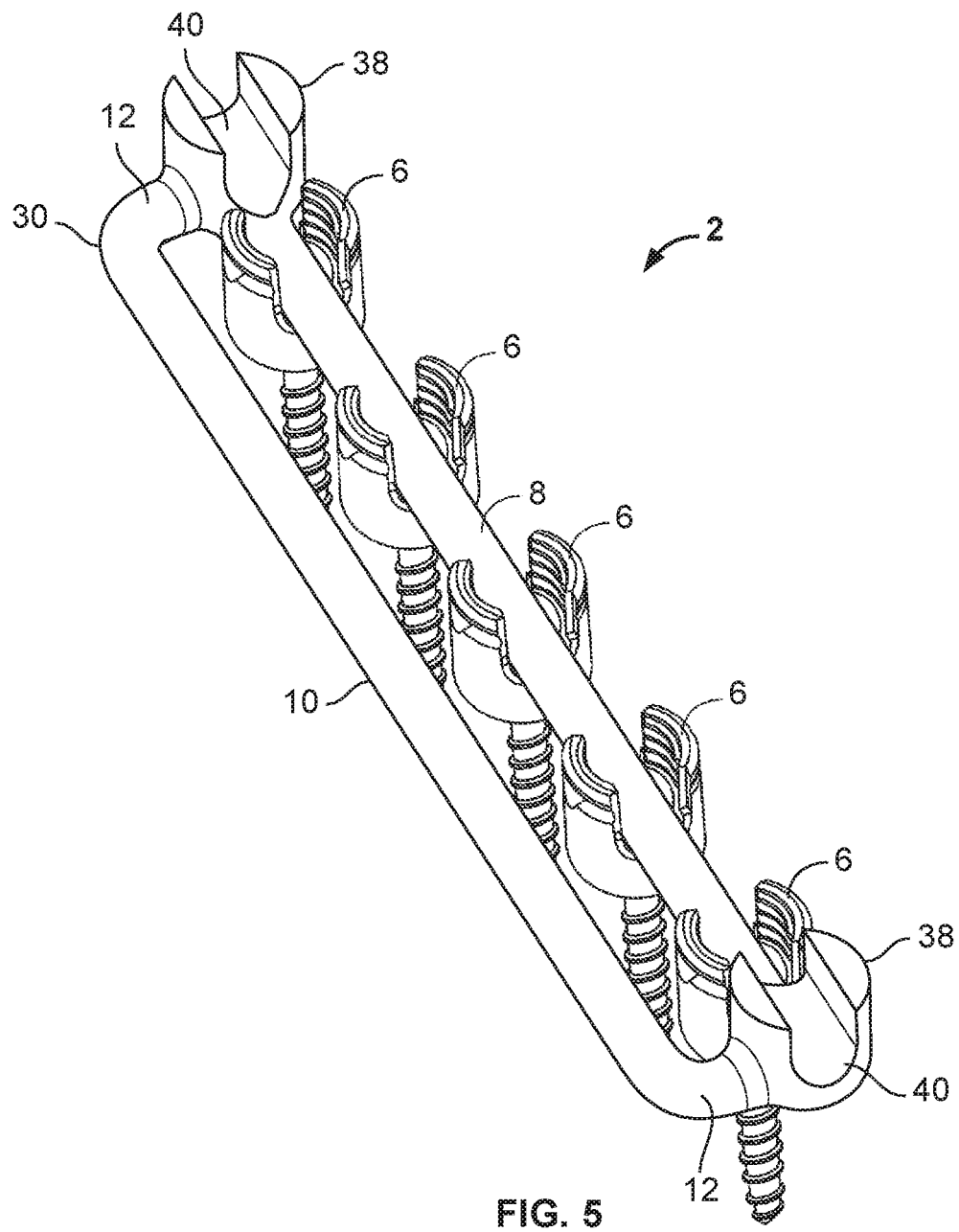
FIG. 5 is a perspective view of a third embodiment of an integral double rod spinal construct.
Figure 6:
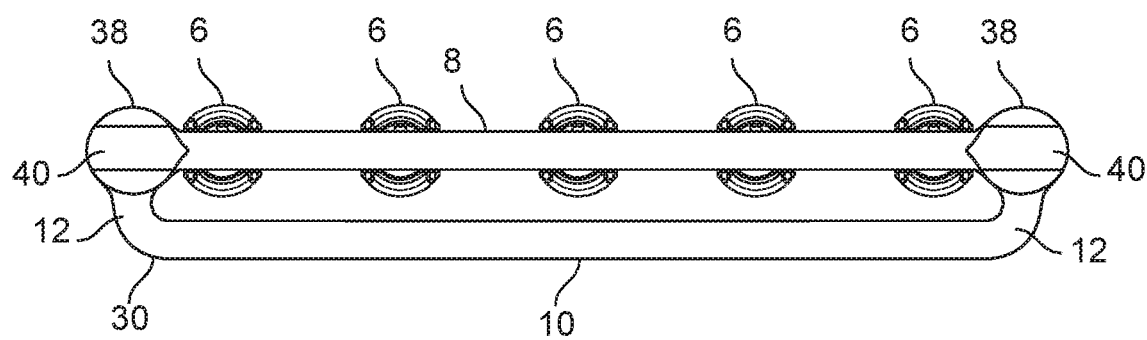
FIG. 6 is a top plan view of the integral double rod spinal construct of FIG. 5.

FIGS. 5-6 illustrate an example of an integral double rod spinal fixation system 2 according to a third embodiment. The integral double rod spinal fixation system of the present example includes an integral double spinal rod 30 and a plurality of bone anchors 6. The integral double spinal rod 30 of the second example includes a first rod 8 and a second rod 10 that is parallel to the first rod 8. The first and second rods 8, 10 are connected to each other by an arm 12 that is integrally formed with the first and second rods 8, 10 such that the first and second rods 8, 10 and arms 12 comprise one single piece of metal. By way of example, the arms 12 are located at each end of the second rod 10 and extend laterally to connect with the first rod 8. By way of example, the first and second rods 8, 10 and arms 12 may be of uniform thickness. The first rod 8 is configured to engage the bone anchors 6 and is therefore generally cylindrical in shape. The first rod 8 further includes integrated rod connectors 38 positioned on either end of the first rod 8. By way of example only, the integrated rod connectors 38 each include a rod seat 40 configured to receive at least a portion of a different spinal rod. The integrated rod connectors 38 may be any type of connectors suitable for connecting to additional rod hardware. The integrated rod connectors 38 may be in-line or offset relative to the first rod 8. In some embodiments, the integrated rod connectors 38 may be in-line with the second rod 10. The integrated rod connectors 38 may be a top loading tulip configuration as shown by way of example in FIGS. 5 & 6 or, alternatively, may be a side loading tulip or a closed head connector of the adjacent rod. Thus, the integrated rod connectors 38 enable connection to additional hardware in longer spine stabilization constructs, for example larger deformity or trauma cases. Additionally, the integral double spinal rod 30 of the present example may be used with an adjacent rod during the primary surgery or implanted with the anticipation of adjacent level surgery in the future. The second rod 10 may have any cross-sectional shape, and primarily functions to provide stability and rigidity to the construct, however, the second rod 10 may also be used as an attachment point for additional hardware or for bending, etc.

It will be appreciated that an embodiment of the dual rod construct may comprise a combination of the elements described in the embodiments of FIGS. 1-6. For example, in one exemplary embodiment, a spinal fixation construct 2 comprises a first spinal rod 8; a second spinal rod 10 generally parallel to the first rod; a cephalad arm 12 connecting the first and second rods 8, 10 and integrally formed with the first and second rods 8, 10; and a caudal arm 12 connecting the first and second rods 8, 10 and integrally formed with the first and second rods 8, 10. The first rod 8 may be generally cylindrical in shape. In some embodiments, the first rod 8 may be uniform in diameter from the cephalad to the caudal arm 12. In some embodiments, the first and second rods 8, 10 may be of uniform thickness.

The construct 2 may further comprise a rod extension 28 extending longitudinally from the cephalad end, from the caudal end, or from both the cephalad and caudal ends. The construct 2 may further comprise a rod connector 38 with a rod seat 40 sized and configured to receive a portion of a third spinal rod (not shown). In some embodiments, the rod connector 38 may be aligned with the first rod. In other embodiments, the rod connector 38 may be aligned with the second rod. And, in still further embodiments, the rod connector 38 may be offset from the first and second rods.

In some embodiments, the construct comprises a rod connector 38 at the cephalad end. In other embodiments, the construct comprises a rod connector 38 at the caudal end. In still further embodiments, the construct comprises a rod connector 38 at both the cephalad and caudal ends. In one embodiment, the rod seat 40 is generally parallel with the first spinal rod. In some embodiments the rod connector 38 is formed integrally with the spinal fixation construct. In some embodiments, the rod connector 38 is top-loading. In other embodiments, the rod connector 38 is side-loading. The rod connector 38 may comprise a tulip. Alternatively, the rod connector 38 may comprise a closed head.

The construct may further comprise a plurality of bone anchors 6 with upstanding arms defining a rod channel 22 dimensioned to accommodate the first rod. The bone anchors 6 may be pedicle screws. In some embodiments, the pedicle screws may be polyaxial. Additionally, the first rod 8 should be of sufficient length between the cephalad and caudal arms 12 to accommodate a plurality of bone anchors 6. Further, the distance between the first and second rods 8, 10 should be sufficient to allow the first rod 8 to be seated in the rod channel 22. When the first rod 8 is seated in the rod channel 22, the rod 8 may be secured with a plurality of locking screws (not shown). In each embodiment, the dual spinal rod 2 is constructed entirely from a rigid, non-absorbable biocompatible material.

Although each of the embodiments depicted in FIGS. 1-6 shows the dual rod 2 engaging five bone anchors 6, it will be appreciated that the actual number of bone anchors 6 will vary according to the surgical procedure, the number of levels involved, and the preferences of the surgeon. Moreover, it will be appreciated that the construct 2 may be placed such that the second rod is located medially or laterally relative to the first rod and bone anchors 6. The position of the second rod 10 may depend upon the surgical procedure, preference of the surgeon, or requirements of a patient's anatomy.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 and related laws or otherwise to provide organizational queues. These headings shall not limit or characterize the invention(s) set forth herein.

What is claimed is:

1. A method of stabilizing a relative position of a first vertebra and a second vertebra in a spinal procedure, the method comprising:
    implanting a plurality of pedicle bone anchors, one each into a plurality of desired pedicle locations on the first vertebra and the second vertebra, each pedicle bone anchor in the plurality of bone anchors including a rod housing;
    providing a dual rod spinal fixation construct, the dual rod spinal fixation construct including:
        a first spinal rod,
        a second spinal rod substantially parallel to the first spinal rod,
        a cephalad arm connecting the first and second spinal rods, and
        a caudal arm connecting the first and second spinal rods,
        the first spinal rod further including a first rod extension extending longitudinally from a first, distal end of the first spinal rod, beyond the cephalad arm and adapted to connect to additional hardware,
        the first spinal rod, the second spinal rod, the cephalad arm, and the caudal arm all being integrally formed with one another;
    bending the first spinal rod to facilitate proper seating of the first spinal rod in the rod housing of each of the plurality of bone anchors;
    seating the first spinal rod in the rod housing of each of the plurality of bone anchors; and
    engaging a lock screw with each of the plurality of bone anchors, wherein the lock screw has a complementary fit with the bone anchor such that the lock screw secures the bent first spinal rod of the dual rod spinal fixation construct in the rod housing of each of the plurality of bone anchors.

2. The method of claim 1, further comprising, prior to the seating, placing the dual rod spinal fixation construct in a generally cephalad-caudal orientation.

3. The method of claim 2, wherein the dual rod spinal fixation construct is placed such that the second spinal rod is oriented medially relative to the first spinal rod.

4. The method of claim 2, wherein the dual rod spinal fixation construct is placed such that the second spinal rod is oriented laterally relative to the first spinal rod.

5. The method of claim 1, further comprising bending the second spinal rod at the same time as bending the first spinal rod.

6. The method of claim 1, further comprising bending the second spinal rod to the same degree as the first spinal rod.

7. The method of claim 1, wherein the dual rod spinal fixation construct further comprises one or more non-absorbable biocompatible materials, and wherein the non-absorbable biocompatible material includes titanium, an alloy of titanium, steel, or stainless steel.

8. The method of claim 1, wherein the cephalad arm connects a first, distal end of the first spinal rod to the first, distal end of the second spinal rod, and wherein the caudal arm connects a second, proximal end of the first spinal rod to the second, proximal end of the second spinal rod.

9. The method of claim 1, wherein the first spinal rod, the second spinal rod, the caudal arm, and the cephalad arm have substantially uniform cross-sectional thickness.

10. The method of claim 1, wherein the first spinal rod has a substantially circular cross section.

11. The method of claim 1, further comprising coupling another spinal fixation construct to the first rod extension.

12. The method of claim 1, wherein the first spinal rod further includes a second rod extension extending longitudinally from a second, proximal end of the first spinal rod, beyond the caudal arm.

13. The method of claim 12, further comprising coupling another spinal fixation construct to the second rod extension.

14. The method of claim 1, further comprising coupling a second spinal fixation construct to the second spinal rod.

15. The method of claim 1, wherein the implanting further comprises implanting five bone anchors.

16. The method of claim 1, further comprising implanting the plurality of bone anchors, one each into a plurality of desired pedicle locations on the first vertebra, the second vertebra, and a third vertebra.

17. The method of claim 16, further comprising implanting the plurality of bone anchors, one each into a plurality of desired locations on the first vertebra, the second vertebra, the third vertebra, and a fourth vertebra.

18. The method of claim 1, wherein the spinal procedure comprises a pedicle subtraction osteotomy (PSO).

* * * * *